Figure 1:
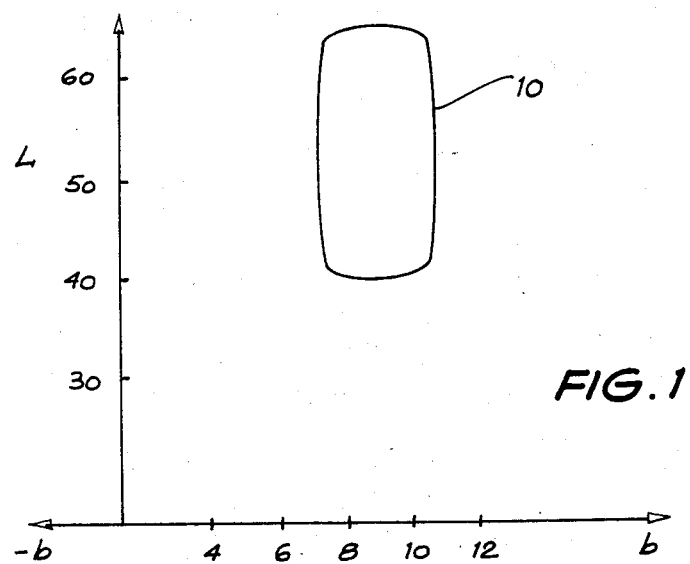

United States Patent [19]

Hall

[11] Patent Number: 4,657,399

[45] Date of Patent: Apr. 14, 1987

[54] COLOR MIXTURE INDICATOR DEVICE

[76] Inventor: Neil R. Hall, 14 Kintore Street, Wahroonga, New South Wales 2076, Australia

[21] Appl. No.: 685,329

[22] Filed: Dec. 21, 1984

[30] Foreign Application Priority Data

Dec. 23, 1983 [AU] Australia .............................. PG3002

[51] Int. Cl.⁴ ............................................... G01J 3/52
[52] U.S. Cl. ....................................... 356/421; 433/26
[58] Field of Search ............... 356/421, 422, 423, 424; 434/98, 99, 100; 433/26

[56] References Cited

U.S. PATENT DOCUMENTS

| 2,009,943 | 7/1935 | Munsell et al. | 356/421 |
| 2,805,478 | 9/1957 | Adams | 433/26 |
| 3,384,983 | 5/1968 | Olson | 434/98 |
| 3,436,156 | 4/1969 | Adler et al. | 356/422 |
| 3,436,157 | 4/1969 | Adler et al. | 356/423 |
| 3,474,546 | 10/1969 | Wedlake | 434/98 |
| 4,523,852 | 6/1985 | Bauer | 356/421 |

FOREIGN PATENT DOCUMENTS 0006352 1/1980 Japan ................................. 356/423

OTHER PUBLICATIONS

Hendrickson, *Information Display*, V. 11, N. 6, Jun., 1975, p. 22.
New Trubyte Shades brochure, 11/30/36.

Primary Examiner—F. L. Evans
Attorney, Agent, or Firm—Berman, Aisenberg & Platt

[57] ABSTRACT

The present invention discloses a set of dental color indicator devices and a method of selecting dental colors. Each indicator device has a number of color samples arranged in a regular array. Each of the samples corresponds to the color at a corresponding location in an identical array formed on one of a plurality of transverse parallel cuts through an elongate substantially elipsoid body which represents the possible range of dental colors when graphically represented on a color co-ordinate system, such as the CIELAB psycometric color system or the Munsell visual color system. The selected color is either the color of one of the samples or a mixture of the color of two adjacent samples.

12 Claims, 10 Drawing Figures

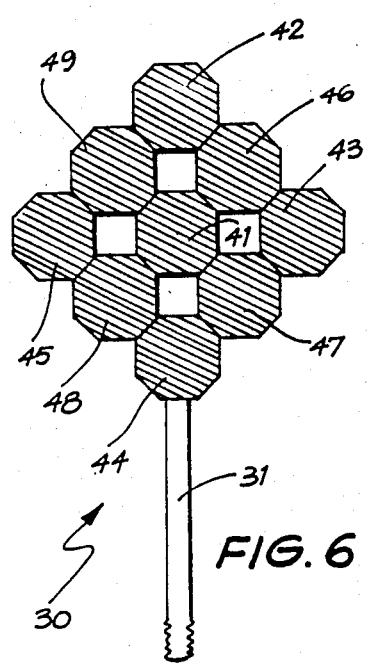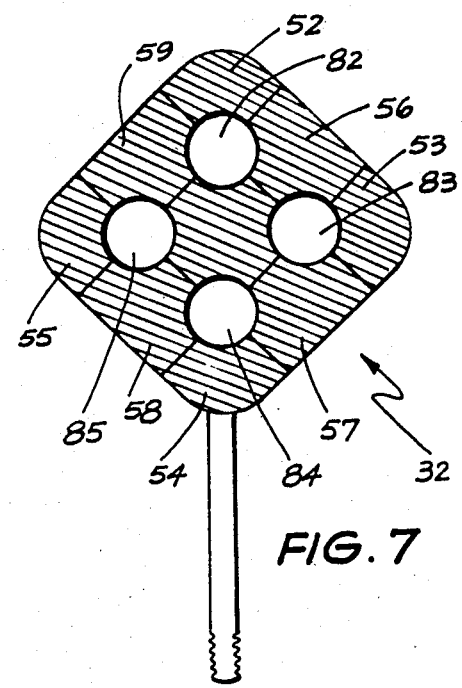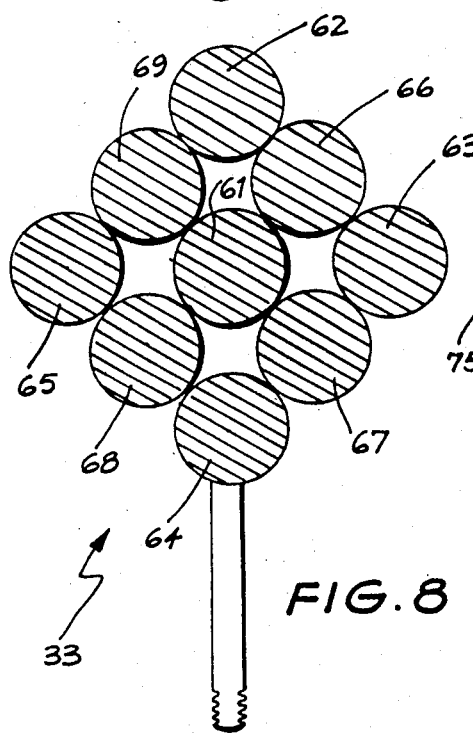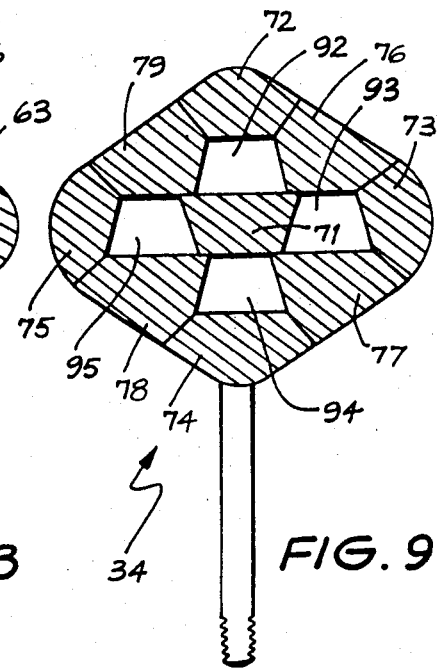

COLOR MIXTURE INDICATOR DEVICE

The present invention relates to dentistry and, in particular, to a colour mixture indicator device which finds particular application in the selection of desired artificial tooth colouring in the fabrication of bridges, crowns, partial dentures, and the like.

In the construction of bridges, partial dentures, and similar artificial tooth structures it is necessary to select a tooth colouring for the artificial tooth which as closely as possible matches the colouring of the remainder of the patient's teeth. The selection of a correctly matching colour is of vital importance since any mismatching has an extremely deleterious effect on the appearance of the patient.

Hitherto, the section of the desired colour has been to some extent a matter of luck and has been very strongly dependent upon the skill of the dentist. In order to assist the dentist, the manufacturers of the powdered ceramic materials, from which the artificial teeth are to be constructed by a dental technician, provide a series of artificial teeth for comparison purposes. This series of teeth is produced in a range of colours which has been developed over the years but basically comprises commercially successful colours.

This situation gives rise to two particular difficulties. The first is that it is difficult to hold the artificial tooth against the remainder of a patient's teeth and achieve a good indication of colour without considerable skill and experience in this selection. Secondly, and most importantly, if the dentist decides that the desired colour for the teeth to be constructed for a patient, is intermediate the colour of two of the sample teeth, then the dentist instructs the dental technician to make the patient's teeth by means of mixing the powdered ceramic materials provided by the manufacturer which correspond to the two selected sample teeth.

The difficulty with this instruction is that the sample teeth are themselves laminated with mixtures of colours and that there is no colour relationship between the sample teeth. That is to say there is no particular gradation between sample teeth as regards chroma, hue, intensity and the like, and no regular arrangement in colour space or colour co-ordinates.

In consequence, it is very difficult to select required mixtures of colours and when the powdered ceramic materials of the two selected sample teeth are mixed together to form a patient's tooth, the resulting colour of the patient's tooth does not necessarily fall between the colours of the sample teeth. Thus although the correct samples may have been selected, the resulting colour is not the intended intermediate colour. Since the fabrication of the artificial teeth is relatively expensive, the patient merely has to be satisfied with whatever result is achieved. In practice there is no possibility to make a replacement if the resulting colour is not correct.

It is the object of the present invention to overcome, or substantially ameliorate, the abovementioned disadvantages by the provision of a colour mixture indicator device which both assists the dentist in the selection of the desired tooth colour and also permits proper colour mixing where necessary to achieve a selected colour.

According to one aspect of the present invention there is disclosed a dental colour mixture indicator device comprising a plurality of colour samples mutually spaced apart to form an array with the colour of each of said samples being representative of the colour of a predetermined colour co-ordinate system at a co-ordinate location corresponding to the location of said sample on said array, whereby a desired dental colour intermediate a selected pair of said colour samples can be mixed for fabrication by a mixture of the colouring materials used to fabricate said selected pair.

Figure 2:
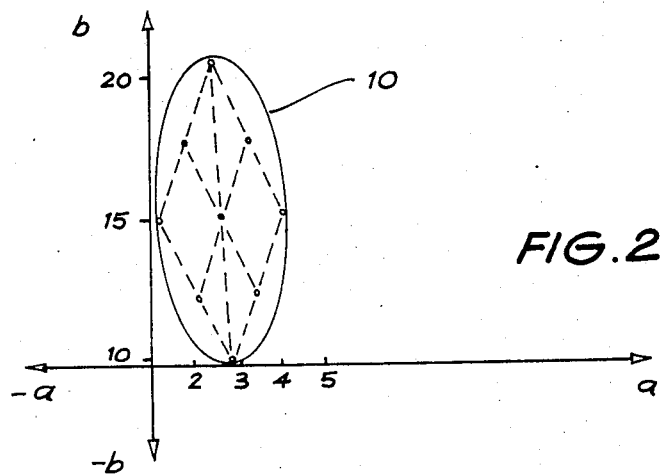
Figure 3:
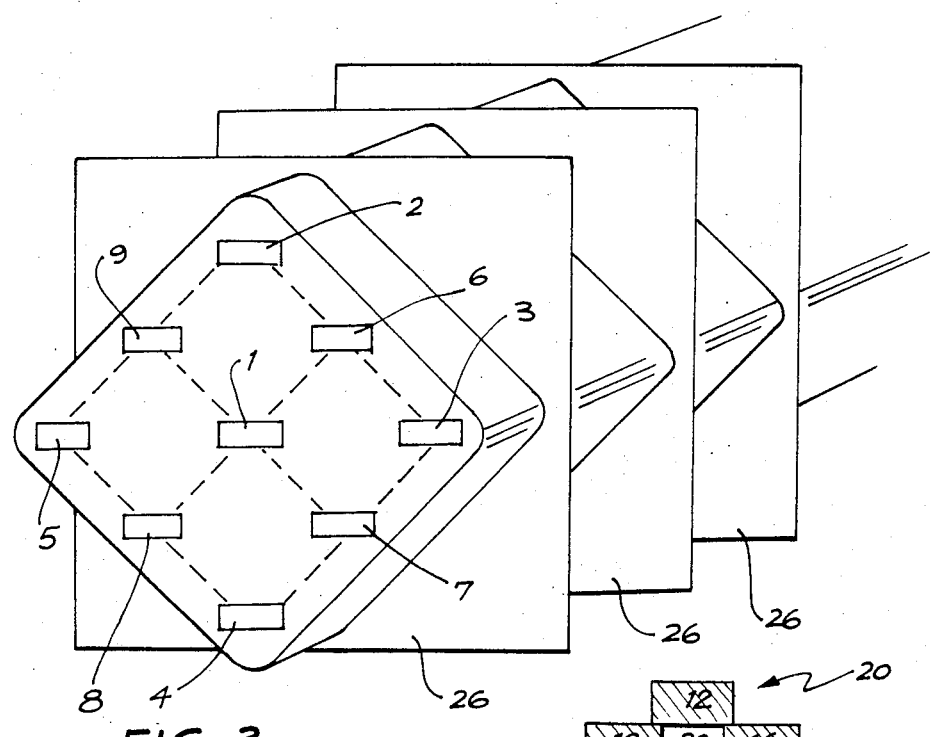
Figure 4:
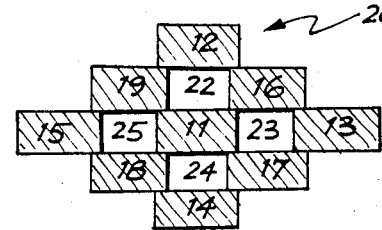
Figure 5:
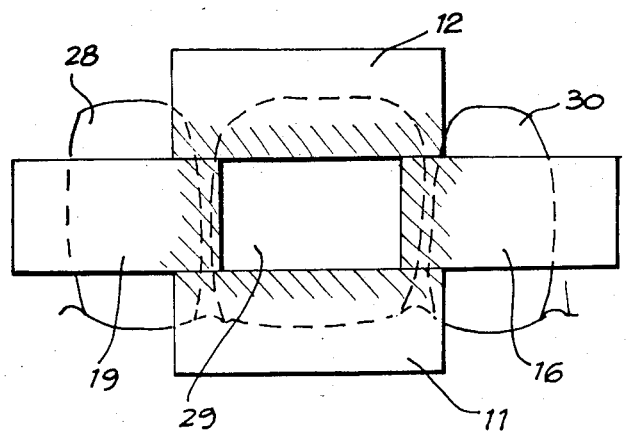
Figure 10:
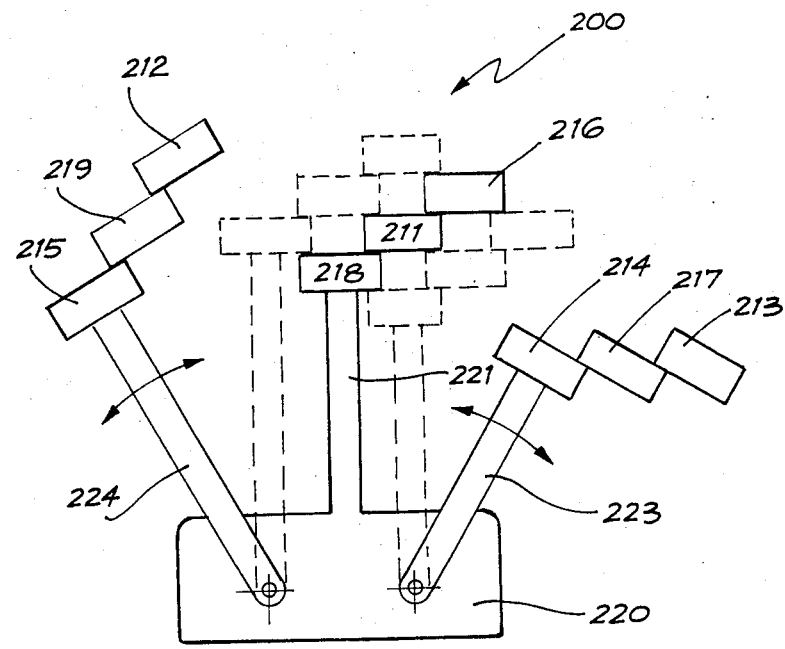

One embodiment of the present invention will now be described with reference to the drawings in which:

FIG. 1 is a representation of the possible range of dental colours in a first, "vertical", plane of a visual colour system, FIG. 2 is a representation in a second "horizontal" co-ordinate plane of the same range of dental colours, FIG. 3 is a schematic perspective view of the colour body of FIGS. 1 and 2 represented in a different co-ordinate system, FIG. 4 is a front elevation of the colour mixture indicator device of a first embodiment, FIG. 5 illustrates how the device of FIG. 4 is held over a patient's teeth for comparison purposes, allowing part of a tooth to be viewed while the rest is obscured, FIGS. 6 to 9 are each views similar to FIG. 4 but of a different embodiment of the indicator device, and FIG. 10 is a view similar to FIG. 4 but of a still further embodiment of the indicator device.

The development of the indicator device of the preferred embodiment is based upon the realization that if the range of dental colours is represented on a visual colour system, then the range of colours falls within a substantially sausage like, or elipsoid, body. The Munsell system, described in detail in the basic application, No. PG 3002 the disclosure of which is hereby incorporated by cross-reference, represents colours in a three-dimensional radial co-ordinate system. The radial co-ordinate is CHROMA, the circumferential co-ordinate is HUE, and the vertical co-ordinate is VALUE. However, this radial co-ordinate system suffers from a number of disadvantages, primarily because like distances between pairs of adjacent points do not necessarily represent like changes in colour.

Thus the preferred form of three-dimensional colour system is a cartesian colour system having a uniform colour scale such as the CIELAB psychometric colour system. In this system the majority of the range of dental colours fall within the substantially elipsoid body 10 illustrated in FIGS. 1 to 3. The CIELAB system represents colours in a three-dimensional cartesian co-ordinate system in which the "horizontal" chromaticity co-ordinates are a (positive representing red and negative representing green) and b (positive representing yellow and negative representing blue). Thus the positive and negative portions of the horizontal axes represent opposed colours. In this system the "vertical" axis represents luminance.

As seen in FIGS. 1 and 2 the body 10 of possible dental colours has an L (luminance) range of approximately 15 units, an a range (red) of approximately 4 units, and a b range (yellow) of approximately 7 units.

Since the longitudinal axis of the body 10 of FIGS. 1 and 2 lies substantially parallel to the vertical luminance axis, the body 10 can be transversely cut at a number of spaced apart locations with each of the cuts lying substantially in a horizontal plane which is parallel to the a, b plane.

FIG. 3 illustrates in schematic perspective fashion this horizontal cutting action with each of the horizontal cuts 26 being spaced apart by the same distance. For ease of illustration the longitudinal axis of the body 10 has been drawn horizontally so that in FIG. 3 each of the cuts 26 (which lie in a plane parallel to the a, b plane of FIG. 2) appears to be vertical.

As seen in FIG. 3 each of the cuts 26 (only one being illustrated in detail) will enable selection of a central colour 1, and four peripheral colours 2 to 5. Each of the peripheral colours 2 to 5 can be notionally joined by a broken line and midway between each pair of the peripheral colours 2 to 5 on these broken lines is located a corresponding one of four interior colours 6 to 9. Because the cut 26 of FIG. 3 is parallel to the a, b plane of FIG. 2, the spacing or distance between each of the pairs of adjacent colours 1 to 9 is substantially 2 $\Delta$ E units where $\Delta$ E is the unit of the scale of the horizontal axes of the CIELAB colour system. That is, this distance between colours 9 and 2 is substantially equal to the distance between colours 1 and 8, and is substantially equal to the distance between colours 6 and 3 with all of these distances being approximately 2$\Delta$ E units.

As a consequence of this selection of colours, it will be apparent to those skilled in the art that each of the interior colours 6 to 9 can be created and reproduced by a mixture of the corresponding pair of peripheral colours 2 to 5. Thus, for example, the interior colour 6 can be formed by mixing equal parts of the peripheral colours 2 and 3 together.

Turning now to FIG. 4, for each of the cuts 26 of FIG. 3 (there being preferably five such cuts), nine colour samples 11 to 19 of artificial tooth material, each corresponding to a corresponding one of the colours 1 to 9, are formed into a colour mixture indicator device 20 having a handle 21.

The colour samples 11 to 19 are each approximately 6 mm in height by 10 mm in width and are arranged in an array corresponding to the co-ordinate location of the corresponding colours 1 to 9. The colour samples 11, 12, 13, 14 and 15 are made from the powdered ceramic artificial tooth material representing the corresponding colours 1, and 2 to 5. The colour samples 16 to 19 are created from mixing the material of samples 2 and 3, 3 and 4, 4 and 5, and 5 and 2 respectively. Once prepared, the colour samples 11 to 19 are placed together as illustrated in FIG. 4 and the coloured material fused to create both the artificial teeth material and hold the samples 11 to 19 together. It will be apparent that the samples 11 to 19 are supported by a handle 21 and create four spaces 22 to 25. Each of these spaces 22 to 25 is approximately the width of a tooth (particularly the front incisors which are the most visible teeth) and is approximately one-half the height of such a tooth. This dimensional arrangement is of assistance to the dentist since a single incisor can be viewed and the colour of a tooth tends to vary from the top half to the bottom half of the tooth.

In assessing the desired colour for the artificial teeth to be fabricated for a patient, the dentist selects one of the (preferably) five colour mixture indicator devices 20 (there being one device 20 for each of the cuts 26 of FIG. 3) and holds same against the existing or remaining teeth 28, 29 and 30 of the patient as indicated in FIG. 5. It will be apparent from FIG. 5 that the size of the colour samples 11 to 19 and the spaces 22 to 25 facilitate the colour comparison since, for example, all the colours 2, 6, 1 and 9 of the corresponding samples 12, 16, 11 and 19 can be directly compared with the colour of tooth 29. If neither of these colours is an exact match, then an evaluation of the mixture of colours 1 and 2, for example, can be made by estimating the resultant colour formed from a mixture of colour samples 11 and 12.

If none of the colours of a particular device 20 appear to match the patient's teeth then a different device 20 can be selected corresponding to a different cut 26. It will be apparent that for each indicator device 20 of the set of indicator devices, the colours will range in chromaticity with various degrees of saturation of yellow and red from colour sample 12 to colour sample 14 of the device 20.

It will also be apparent to those skilled in the art that once the correct indicator device 20 has been selected, the desired tooth colour can be quickly ascertained since each of the samples 11–19 are chromatically related. This is not the case with the prior art artificial tooth samples of commercially successfully colours. Thus the dentist can specify either that the artificial tooth is to be made from one of the nine colour samples of a particular indicator device, or that it is to be made from a mixture of two of the colour samples 11 to 19 of a particular indicator device 20. In so specifying a mixture, the dentist can be confident that the resultant colour will in fact be a mixture of the two colours of the selected pair of samples. This will be apparent from FIG. 5 since substantially identical resultant colours will be produced irrespective of whether the desired colour to be mixed is specified as being a mixture of colours 2 and 1 (i.e. samples 11 and 12) or colours 9 and 6 (i.e. samples 19 and 16).

A further advantage of the present arrangement is that the dental technician need only stock a limited supply of colours. That is, for each of the preferred five cuts 26, the dental technician need only stock the peripheral colours 2 to 5. The remaining interior colours 1 and 6 to 9 can be manufactured from a combination of those stock colours, as can be any specified two colour combination of the central colour 1, the peripheral colours 2 to 5 and the interior colours 6 to 9. Since for each of the five cuts, only four colours need be stocked, the dental technician need only stock 20 colours in order to substantially completely cover the range of possible dental colours.

Once the theoretical basis for the cuts 26 and colours 1 to 9 is established it will be apparent that a suitable indicator device can take many forms other than the indicator device 20 of FIG. 4. Thus, as seen in FIG. 6, another indicator device 30 having a handle 31 and nine samples 41 to 49 is easily constructed with the samples 41 to 49 being of substantially hexagonal shape.

FIGS. 7, 8 and 9 respectively indicate alternative constructions for indicator devices 32, 33 and 34 each with nine colour samples 51 to 59, 61 to 69 and 71 to 79 respectively. The indicator 33 has substantially circular colour samples 51 to 59. The indicator 32 has four substantially circular spaces 82 to 85. The indicator 34 has four substantially trapezoid spaces 92 to 95. However in all instances although the colour samples can be of any shape, to reflect the corresponding colours within the colour body 10, the colour samples should be arranged in the indicated pattern which allows a viewing arrangement of the type as described in relation to FIG. 5.

Turning now to FIG. 10, an alternative arrangement for the indicator device of FIG. 4 is illustrated. Here the device 200 has a base 220 and a fixed handle 221 which supports three samples 218, 211 and 216. In addition the base 220 has two pivoted handles 222 and 223 which are pivoted at 224 and 225 respectively so as to be movable in the arcs indicated by the two arrows in FIG. 10.

Handle 223 supports three colour samples 214, 217 and 213 which are joined together. Handle 224 suports colour samples 215, 219 and 212 which are joined together. FIG. 10 illustrates the handles 223 and 224 pivoted away from the fixed handle 221 and the situation where the handles 223 and 224 are substantially parallel is indicated by broken lines.

It will be apparent that the arrangement of FIG. 10 allows the colour samples of the indicator device 200 to be moved apart in groups of three as a further aid in comparison of the colours of the samples, say, 218, 211 and 216 with the colour of the patient's teeth.

Thus the device 200 in use, enables the dentist or dental technician to more easily compare a pair of colours (i.e. the patient's tooth and one of the colour samples) as he is used to doing with conventional samples of commercially successful colour guides. The direction of the "split up" of the indicator device 200 is selected because in practice it has been found that variation in tooth colour is in the direction of colour samples 215, 219, 212.

The foregoing describes only one embodiment of the present invention and modifications, obvious to those skilled in the art, can be made thereto without departing from the scope of the present invention.

What I claim is:

1. A dental colour mixture indicator device comprising a plurality of colour samples located in an array with each sample spaced apart from samples adjacent thereto to define an inter-sample space, with the colour of said samples being representative of colours of a predetermined colour system having a co-ordinate system aligned with said array wherein the colour of each of said samples corresponds to the colour of the corresponding location in said co-ordinate system, so that a patient's tooth can be viewed through said inter-sample space and a desired dental colour intermediate a selected pair of said colour samples can be mixed for fabrication by a mixture of the colouring materials used to fabricate said selected pair.

2. An indicator device as claimed in claim 1 wherein said array is a substantially rectangular grid.

3. An indicator device as claimed in claim 2 having nine of said colour samples separated by four spaces.

4. An indicator device as claimed in claim 3 wherein said colour samples have a shape selected from the group of shapes consisting of rectangles, hexagons, circles and trapezoids.

5. An indicator device as claimed in claim 3 wherein said spaces have a shape which is rectangular, circular or trapezoidal.

6. An indicator device as claimed in any one of claims 1 to 4 or 5 wherein said colour samples are mounted on a handle.

7. An indicator device as claimed in any one of claims 1 to 4 wherein said colour samples are mounted on a handle and a group of said colour samples is movable with respect to another group of said colour samples.

8. A set of dental colour mixture indicator devices, said set comprising a plurality of the indicator devices of claim 1 wherein the colours of the samples of each said device are located on a plane of said co-ordinate system and the plane corresponding to each device is substantially parallel to, and spaced from, the planes of the other ones of said device.

9. A set of indicator devices as claimed in claim 8 wherein said planes are substantially equally spaced apart and each colour sample in each said plane is substantially equally spaced apart from its adjacent colour samples.

10. A method of selecting a dental colour from an elongate body of possible dental colours represented on a colour co-ordinate system, said body having a longitudinal axis, said method comprising the steps of notionally cutting said body transverse to said axis with a plurality of substantially parallel cuts, notionally locating a regular grid of lines on each of said cuts, said lines having intersections forming an array of locations, selecting for each cut a plurality of colours, each of said colours lying at a corresponding intersection location of the grid on said cut and selecting the desired shade of said dental colour by firstly selecting one of said cuts, and secondly selecting the desired shade to be either one of said selected colours for the selected cut or a colour mixture of two adjacent ones of said selected colours for the selected cut, the selection of said selected cut being accomplished by selecting one indicated device of a set of indicator devices comprising a plurality of the indicated devices of claim 1 wherein the colours of the samples of each said device are located on a plane of said co-ordinate system and the plane corresponding to each device is substantially parallel to, and spaced from, the planes of the other ones of said device, and the selection of the desired shade is accomplished by comparing the colour of adjacent ones of the samples of said selected indicator devices.

11. A method of selecting a dental colour from an elongate body of possible dental colours represented on a colour co-ordinate system, said body having a longitudinal axis, said method comprising the steps of notionally cutting said body transverse to said axis with a plurality of substantially parallel cuts, notionally locating a regular grid of lines on each of said cuts, said lines having intersections forming an array of locations, selecting for each cut a plurality of colours, each of said colours lying at a corresponding intersection location of the grid on said cut and selecting the desired shade of said dental colour by firstly selecting one of said cuts, and secondly selecting the desired shade to be either one of said selected colours for the selected cut or a colour mixture of two adjacent ones of said selected colours for the selected cut.

12. In a coloured artificial tooth structure prepared from a mixture of powdered ceramic material, the improvement wherein the colour thereof is that selected in accordance with the method of claim 11.

* * * * *